United States Patent [19]

Sneider

[11] 4,133,313
[45] Jan. 9, 1979

[54] EXPANDABLE SYRINGE

[76] Inventor: Vincent R. Sneider, 3422 Hallcrest Dr. NE., Atlanta, Ga. 30319

[21] Appl. No.: 744,046

[22] Filed: Nov. 22, 1976

Related U.S. Application Data

[63] Continuation-in-part of Ser. No. 591,612, Jun. 30, 1975, Pat. No. 3,993,070.

[51] Int. Cl.² .............................................. A61M 1/00
[52] U.S. Cl. .................................... 128/232; 128/239
[58] Field of Search ................. 128/232, 251, 227, 239

[56] References Cited

U.S. PATENT DOCUMENTS

| 737,795 | 9/1903 | Woud | 128/239 |
|---|---|---|---|
| 770,739 | 9/1904 | Coleman | 128/232 X |
| 845,249 | 2/1907 | Morris | 128/239 |
| 1,155,848 | 10/1915 | Tyrrell | 128/239 X |
| 2,034,926 | 3/1936 | Smith | 128/239 |
| 2,074,438 | 7/1936 | Sinkler | 128/232 X |
| 2,075,577 | 3/1937 | Gerhardstein | 128/232 X |
| 3,354,883 | 11/1967 | Southerland | 128/232 |
| 3,401,695 | 9/1968 | Rosenberg et al. | 128/232 |
| 3,474,788 | 10/1969 | Corbin et al. | 128/227 X |
| 3,916,896 | 11/1975 | Ballard | 128/239 |

FOREIGN PATENT DOCUMENTS 251073  5/1926  Italy ........................................ 128/239

*Primary Examiner*—John D. Yasko
*Attorney, Agent, or Firm*—Hosier, Niro & Daleiden

[57] ABSTRACT

An expandable syringe comprising an elastic bag having an opening through which liquid may pass and a nozzle having a tubular body defining a central passageway and a tip on an end thereof. The nozzle is provided with at least one peripheral port in fluid communication with the tubular body central passageway. A mount is also provided for detachably mounting the nozzle to the elastic bag with the tubular body central passageway in valve controllable fluid communication with the elastic bag opening.

Means for storing and readily obtaining access to a set of individually proportioned and encapsulated chemical agents for successive use with an expandable syringe comprising a case and a unitary slit jacket sized to hold juxtaposed envelopes encapsulating the agents and sized to be slidably received within the case. The jacket has a pair of juxtaposed tabs adapted to be manually gripped in sliding the jacket into and out of the case.

A convertible valve is also disclosed for introducing liquid into a bag from a spout and for expelling liquid from the bag through a syringe nozzle. The convertible valve comprises a tubular valve seat having a radially inward directed flange having an aperture therethrough intermediate the ends thereof. A device is included for securing the valve seat to the bag in fluid communication with an opening in the bag. A bulbous gasket is provided having a tubular section mounted within the valve seat upon the side of the valve seat flange distal the bag, a neck section extending through the valve seat flange aperture, and a flange section mounted upon the valve seat flange proximal the bag. The convertible valve also includes a flexible disc mounted within the valve seat in abutment with the gasket flange portion and having a flap movable between positions closing and opening the end of the gasket neck section proximal the bag.

An expandable syringe is also disclosed in another form comprising an elastic bag and a backing ring secured to an interior surface of the bag. A resilient coupler has a recess sized to receive the backing ring with that portion of the bag overlaying the ring tautly sandwiched between the ring and coupler and an internally threaded tubular throat extending from the recess. A nozzle has an externally threaded end sized to be threadedly inserted into the coupler and into puncturing contact with the tautly sandwiched bag portion.

7 Claims, 12 Drawing Figures

EXPANDABLE SYRINGE

REFERENCE TO RELATED APPLICATION

This is a continuation-in-part of copending application Ser. No. 591,612 filed June 30, 1975 now U.S. Pat. No. 3,993,070.

BACKGROUND OF THE INVENTION

This invention relates to an expandable syringe, and is more particularly concerned with a syringe for providing vaginal douches, enemas and the like.

Vaginal douche devices, and particularly vaginal syringes are well known in the art and in commerce. One general form of syringe includes a substantially flat bag which may be expanded by filling with water or other appropriate liquid. After the liquid has been placed in the bag, a nozzle is inserted into the filling spout of the bag so that the apparatus may be used as a syringe. The expanded bag may be depressed to assist in urging the liquid from the bag, and through the nozzle. One particular syringe of this general description is known as the "Shy" douche device.

While syringes of the above described general type have been used for some considerable length of time and have achieved some commerical success, there are several problems inherent in the design of this type of prior art syringes. Generally, once the nozzle is inserted into the syringe, there is no means for controlling the flow of liquid from the syringe and through the nozzle. When there is pressure because of the introduction of a quantity of liquid under pressure into the syringe, it is possible to inadvertently dispense the liquid upon insertion of the nozzle into the syringe. Also, since the filling spout includes a valve which is openable by either water pressure or the insertion of a nozzle, it is virtually impossible to empty the syringe after usage thereof, and it is equally difficult to rinse any chemicals out of the syringe before the syringe is stored. In addition, the pattern of liquid spray emitted from the nozzle has not been sufficiently controlled nor has the rate of liquid emission been of sufficient magnitude. The prior art syringes have also been of too complex and expensive construction. The syringe nozzles have often been difficult to mount and dismount from the syringe bag. Furthermore, their associated storage facilities for the chemical agents used in the syringes have often been cumbersome to operate in obtaining an individual use portion and of excessively costly construction.

Accordingly, it is a general object of the present invention to provide an improved expandable syringe.

More specifically, it is an object of the invention to provide an expandable syringe with a detachable nozzle from which a directionally controlled liquid spray may be emitted at relatively high rates.

Another object of the invention is to provide an expandable syringe with a convertible valve to which a nozzle for expelling liquid out of, and a fauset spout for introducing liquid into, a syringe bag may be interchangeably coupled.

Another object of the invention is to provide an expandable syringe having an elastic bag with a bag section predesignated to be punctured and thereby opened by and upon the mounting of a syringe nozzle to the bag.

Another object of the invention is to provide expandable syringes of the types just described of relatively simple, dependable and economical construction.

Yet another object of the invention is to provide structurally economic and simple means for storing and for readily obtaining manual access to a set of individually proportioned and encapsulated chemical agents for successive use with expandable syringes of the types described.

SUMMARY OF THE INVENTION

In one form of the invention an expandable syringe is provided comprising an elastic bag having an opening through which liquid may pass, and a nozzle having a tubular body defining a central passageway and a tip formed on an end of the tubular body. The nozzle is provided with at least one peripheral port in fluid communication with the tubular body passageway. The syringe also comprises means for detachably mounting the nozzle to the elastic bag with the tubular body passageway in valve controllable fluid communication with the elastic bag opening.

In another form of the invention, an expandable syringe comprises an elastic bag through which liquid may pass and a unitary, resilient nozzle having a cylindrical, tubular body defining a central passageway extending therethrough. The syringe includes a tip on an end of the tubular body spaced from the central passageway having a plurality of radially spaced peripheral ports. A hub is formed within the tubular body axially between the central passageway and tip. A plurality of radially spaced ribs join the hub with the tubular body to define a plurality of axially extending channels providing fluid communication between the central passageway and the ports. The syringe also includes means for mounting the nozzle to the elastic bag with the central passageway in valved controllable fluid communication with the bag opening.

In another form of the invention an expandable syringe comprises an elastic bag having an opening through which liquid may pass and convertible valve means adapted to be mounted to the bag about the opening for introducing liquid into the bag from a spout and for expelling liquid from the bag through a syringe nozzle. The connectable valve means includes a tubular valve seat having a radially inward directed flange having an aperture therethrough intermediate the ends thereof. Means are provided for securing the valve seat to the elastic bag in fluid communication with the bag opening. A bulbous gasket has a tubular section mounted within the valve seat upon the side of the valve seat flange distal the elastic bag, a neck section extending through the valve seat flange aperture, and a flange section mounted upon the side of the valve seat flange proximal the elastic bag. A flexible disc is mounted within the valve seat in abutment with the gasket flange portion and having a flap movable between a position closing and a position opening the end of the gasket section proximal the elastic bag.

In another form of the invention an expandable syringe is provided comprising an elastic bag and a backing ring secured to an interior surface of the bag. A resilient coupler is provided having a recess sized to receive the backing ring with that portion of the elastic bag overlaying the backing ring tautly sandwiched between the ring and coupler and an internally threaded tubular throat extending from the recess. Also included is a nozzle having an externally threaded end sized to be threadedly inserted into the coupler and into puncturing contact with the tautly sandwiched elastic bag portion.

In yet another form of the invention means are provided for storing and for readily obtaining access to a set of individually proportioned and encapsulated chemical agents for successive use with an expandable syringe or the like comprising a case and a unitary split jacket sized to hold a plurality of juxtaposed envelopes encapsulating indivdual portions of chemical agents and sized to be slidably received within the case. The unitary split jacket has a pair of juxtaposed tabs adapted to be manually gripped in sliding the jacket into and out of the case.

DESCRIPTION OF THE PREFERRED EMBODIMENTS

Figure 1:
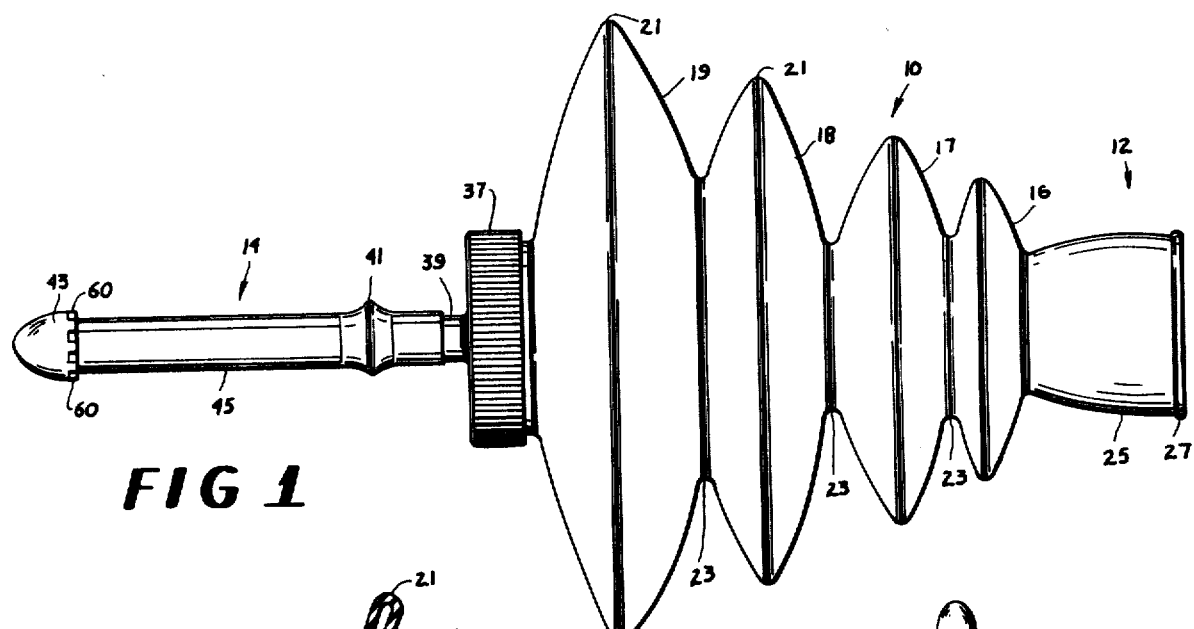
FIG. 1 is a side elevational view of an expandable syringe embodying principles of the invention in one preferred form with the syringe elastic bag disposed in a relaxed, unfolded position.
Figure 2:
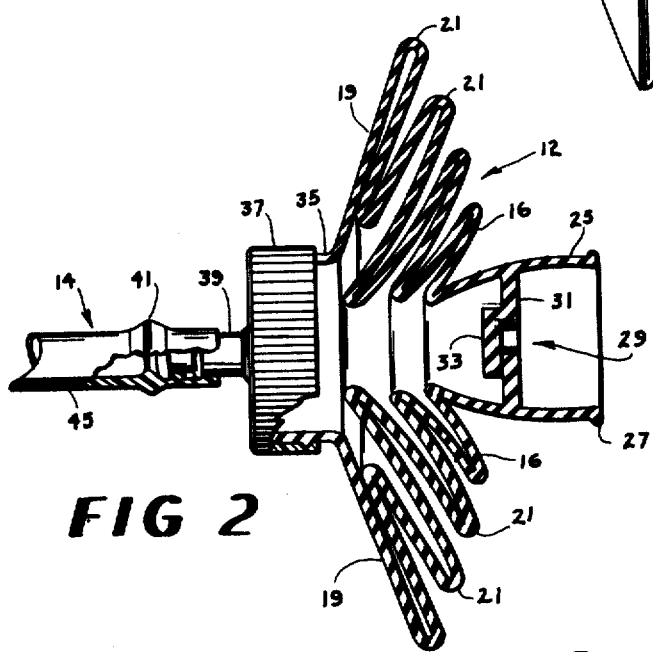
FIG. 2 is another side elevational view of the expandable syringe illustrated in FIG. 1 with the syringe elastic bag shown in cross section in a folded position.
Figure 3:
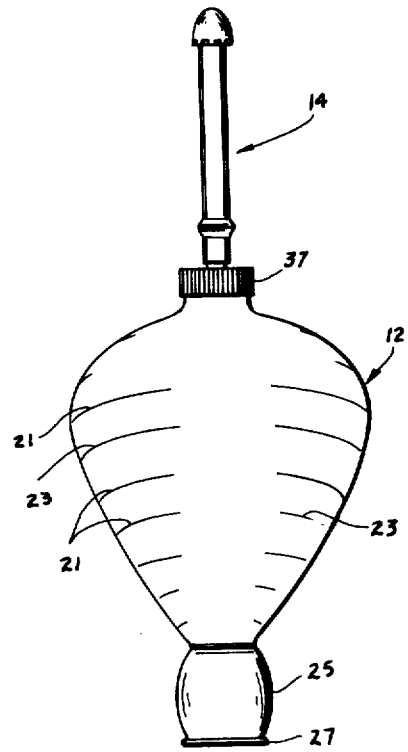
FIG. 3 is another side elevational view of the expandable syringe illustrated in FIG. 1 with the syringe elastic bag shown disposed in an expanded position.

Referring now in more detail to the drawing, there is shown in FIGS. 1-5 an expandable syringe comprising an elastic bag 10 having filling means 12 at one end thereof and a nozzle 14 at the opposite end thereof. The elastic bag, which preferably is formed of rubber or a flexible plastic, is seen to be in the form of a collapsible bellows having four unitarily formed and successively connected bellows sections 16-19 of successively increasing size. The maximum size of each section is attained at an outward fold 21 while the minimum size of each is contiguous with the next successive section attained at an inward fold 23. So constructed, the elastic bag may assume a relaxed position as shown in FIG. 1, a folded position as shown in FIG. 2 or an expanded position as shown in FIG. 3.

From bellows section 16 projects bag filling means 12 which comprises an elastic tube 25 having an annular lip 27 at an open end distal bellows section 16 and a unidirectional valve 29 formed intermediate the tube ends. Valve 29 is composed of a vertically apertued, disc-shaped wall 31 with a disc-shaped flap 33 overlaying the wall aperture with the aperture normally closed. So constructed, bag 10 may be filled with water by telescopically placing tube 25 snuggly over a spout of a water faucet or the like and then turning the faucet on. The pressure of the water upon valve flap 33 forces it to lift off the valve wall thereby opening the valve and permitting entry of the water into the bag.

From bellows section 19 at the opposite end of the elastic bag projects an externally threaded tubular neck 35 having an open end to which an internally threaded cap 37 is secured. The cap is provided with a tubular connector 39 having conventional means for detachably securing nozzle 14 thereto for restricted axial movement with respect thereto for operation of a push-pull valve within an enlarged nozzle compartment 41.

Figure 4:
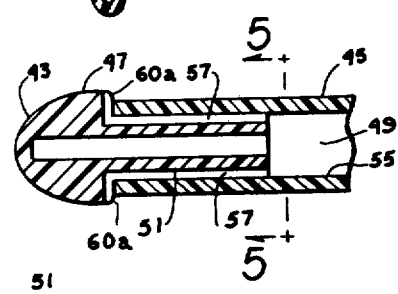
FIG. 4 is an axial cross-sectional view of a portion of the nozzle component of the syringe shown in FIG. 1.
Figure 5:
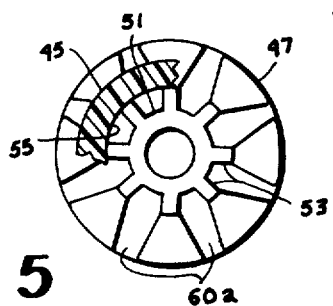
FIG. 5 is a transverse cross-sectional view of the nozzle shown in FIG. 4 taken along plane 5—5.

With particular reference next to FIGS. 4 and 5 the nozzle, which is formed preferably of rubber or plastic, is seen further to have a rounded tip with that portion 47 of the tip proximal a tubular body portion 45 of the nozzle being cylindrical. At an end portion of a central passageway 49 within tube body 45 is formed a cylindrical hub 51 from which a set of radially spaced ribs 53 extend to the interior surface 55 of the tube body in forming a plurality of axially extending channels 57. At one end these channels are in fluid communication with the central passageway 49 while at their opposite end they are in fluid communication with a plurality of radially separated ports 60 formed in cylindrical tip section 47. It should be noted that end portions of these ports are open towards the tubular body portion 45 of the nozzle as well as open radially the nozzle tip. This configuration of the port orifices causes a spray of liquid emitted from the ports to be patterned radially from body portion 45. The purpose of this is to restrict the spray pattern axially forward of tip 43.

In operation, nozzle 14 is moved axially towards the cap thereby placing the push-pull valve with nozzle section 41 in its closed position. The bag filler means elastic tube 25 is then telescopically placed snuggly over a water faucet spout. Water is then pressure forced through valve 29 and into bag 10 there mixing with a chemical agent. When the bag is fully extended, as shown in FIG. 3, the back pressure of the water within the bag will approach the line pressure of the water being emitted from the faucet. As pressure equilization is approached and valve flap 33 closes the faucet is then turned off and the syringe removed. Nozzle 14 may now be inserted into a vagina, rectum or other organ to be cleansed or treated and the end of the nozzle urged away from cap 37 causing the push-pull nozzle valve to open. The liquid solution within the bag is then forced out of the elastic bag into the nozzle central passageway 49, into the several axial channels 57, and radially out of the nozzle tip through ports 60. This action continues until the bag becomes relaxed as shown in FIG. 1 at which time it may be necessary manually to squeeze the bag and the remainder of the solution out of the nozzle until the bag is fully contracted as shown in FIG. 2. The nozzle may then be removed and the syringe flushed clean either with without temporary removal of the nozzle from the cap spout or the assembled cap and nozzle from the bag. The bag may then be compactly stored in its collapsed configuration.

Figure 6:
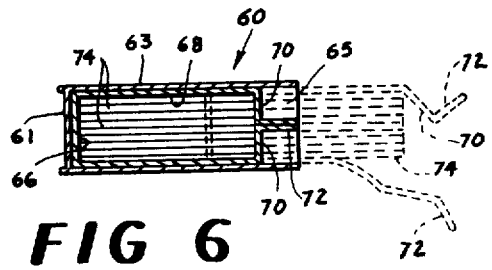
FIG. 6 is a side elevational view of means for storing a set of individually proportional and encapsulated chemical agents with the storage means case and enclosed jacket shown in cross section to reveal a set of encapsulated chemical agents stored therein.

With reference next to FIG. 6 means are shown for storing and for readily obtaining access to a set of individually proportioned and encapsulated chemical agents for successive use with the first described or other type syringe. The storage means here is seen to include a relatively rigid, rectangular case 60 having a bottom 61 and two opposed sides 63 conjoined by two other, opposed sides 65, one of which is shown in the drawing. The top of the case opposite bottom 61 is open in this embodiment and can be closed by a suitable cap (not shown). Within the case is slidably disposed a unitary parallelepiped split jacket formed from a sheet of flexible material such as paper. The jacket has six mutually parallel creases forming six right-angular folds. So formed, the jacket has a bottom 66 from which extend two mutually parallel sides 68 that respectively merge with two coplanar tops 70 from which protect two abutting tabs 72 parallel with each other and with sides 68 when positioned within the case. A set of sealed envelopes 74 containing chemical agent in granulated or liquid form is disposed side by side within the jacket. In use, one may reach into the open end of case 60 and manually grip tabs 72 by placing them between the thumb and index finger. The jacket may be then slid part of the way out of the case and the tabs released. Being flexible, the tabs separate by flopping open to the random position shown in broken lines. This exposes the set of envelopes 74 whereby one envelope may be readily extracted from the set. The jacket may then be reinserted into the case causing tabs 72 to be forced by the case sides 63 back to their juxtaposed position recessed within the bound of the case snuggly about the envelopes.

Figure 7:
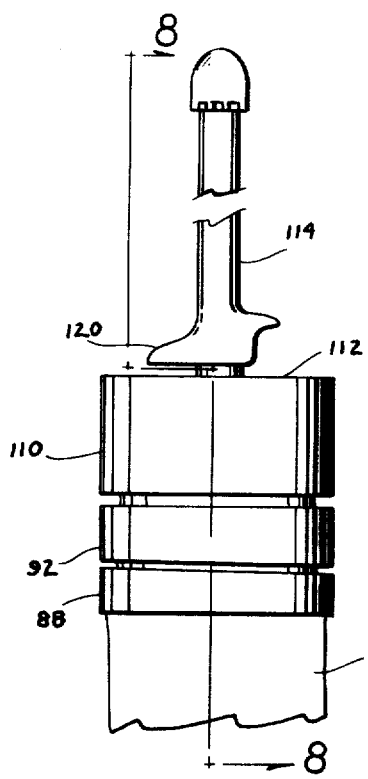
FIG. 7 is a side elevational view of an expandable syringe embodying principles of the invention in another form with a portion of the syringe elastic bag shown broken away.
Figure 8:
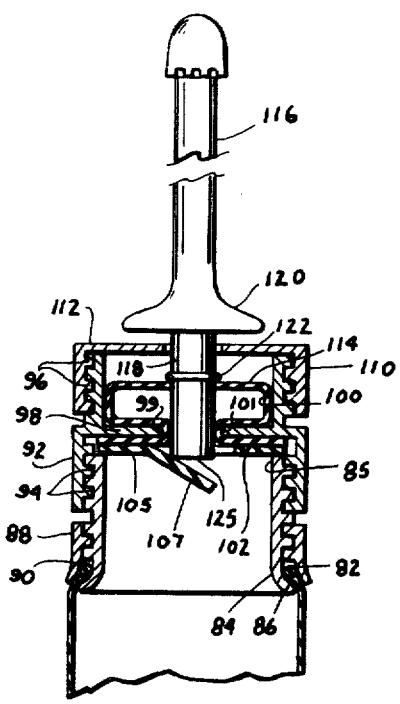
FIG. 8 is a cross-sectional view of the expandable syringe shown in FIG. 7 taken along planes 8—8.

With reference next to FIGS. 7 and 8 another expandable syringe is illustrated having an elastic bag 80 provided with a single opening bounded by bulbous, annular lips 82 through which water or other liquid may be both introduced and expelled. Here, the syringe is seen to include a convertible valve having an externally threaded tubular neck piece 84 with an annular end 85 and an annular groove 86 formed about the end of the neck piece opposite end 85 in which groove is snuggly seated the bulbous annular lips 82 of the elastic bag. An internally threaded retainer ring 88 is mounted about neck piece 84 with an annular ring recess 90 positioned about bag opening lips 82.

A generally tubular valve seat 92 is provided with internal threads 94 on its lower end and external threads 96 on its upper end. The valve seat has a radially inwardly directed flange 98 intermediate the two threaded valve seat ends and a central aperture defined by circular wall 99. A resilient, bulbous gasket is mounted to and within the valve seat with a tubular section 100 upon the side of flange 98 distal the plastic bag, a neck section 101 extending through wall 99, and a flange section 102 mounted upon the side of flange 98 proximal the bag. A flexible disc 105 is mounted within the valve seat sandwiched between and gasket flange section 102 and annular end 85 of the neck piece. The disc has a flap 107 hingedly and unitarilly dispersed within a C-shaped central cut through the disc.

With continued reference to FIGS. 7 and 8, the convertible syringe valve is further seen to include an internally threaded cap 110 threadedly mounted upon the valve seat. The cap has a disc shaped top 112 provided with a central aperture axially aligned with a central aperture in the top 114 of the tubular section 100 of the bulbous gasket. A nozzle 116 is coupled with the cap having a tubular end 118 sized for limited sliding movement through the cap aperture and through the valve seat flange aperture and overlaying gasket neck section 101. Limiting this movement is a nozzle flange 120 positioned outside of cap 110 and an annular rib 122 inside the cap. The body of the nozzle adjacent rib 122 is sized to fit tightly within the central aperture in the top 114 of the flexible gasket thereby forming a sliding seal.

In operation, the cap and nozzle assembly is unscrewed from the valve seat and the spout of a faucet or the like inserted through the aperture in gasket top 114 and firmly onto an interior surface of the gasket tubular section 100 adjacent the aperture in the valve seat flange as shown in broken lines in FIG. 8. The faucet is then opened causing the line pressure of the water to force open valve disc flap 107 and enter the elastic bag. When the bag is filled the convertible valve is withdrawn from the faucet spout whereupon the pressure of water within the bag forces valve flap 107 closed. Cap 110, with nozzle 116 loosely coupled thereto, is then screwed upon the valve seat. The nozzle is then placed in operative position and if nozzle flange manually moved against the top of cap 110. This action causes the nozzle end 125 to force valve flap 107 open whereby the water exits the syringe bag and nozzle.

Figure 12:
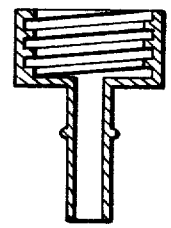
FIG. 12 is a cross-sectional view of an adapter for the expandable syringe of FIGS. 7 and 8, for use with a screw-type nozzle.

Referring to FIGS. 8 and 12, the nozzle 116 may also be of the screw-type having an external threaded end. In this instance, an adapter as shown in FIG. 12, may be inserted in lieu of the nozzle 116 through the adapter in the cap 110, narrow end first. The adapter operates in the same manner as the nozzle 116 and receives the external threads of a screw-type nozzle.

Figure 11:
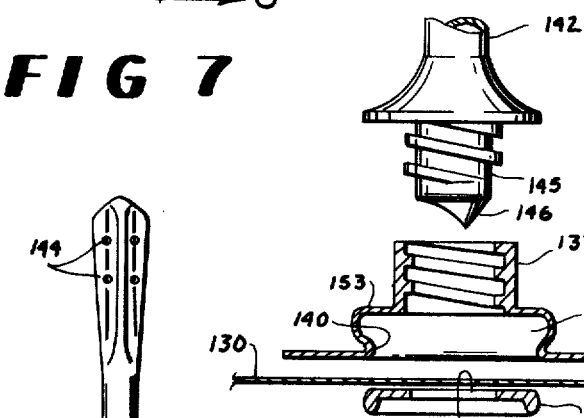
FIG. 11 is a cross-sectional view taken along plane 10—10 of a portion of the syringe elastic bag and nozzle coupler means of FIG. 9 in an assembled condition together with a side elevational view of a portion of the syringe nozzle of FIG. 9.
Figure 10:
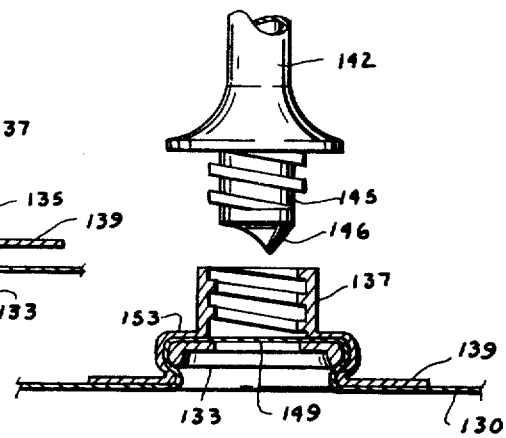
FIG. 10 is a cross-sectional view taken along plane 10—10 a portion of the syringe elastic bag and nozzle coupler means of FIG. 9 in an unassembled condition together with a side elevational view of a portion of the syringe nozzle of FIG. 9.
Figure 9:
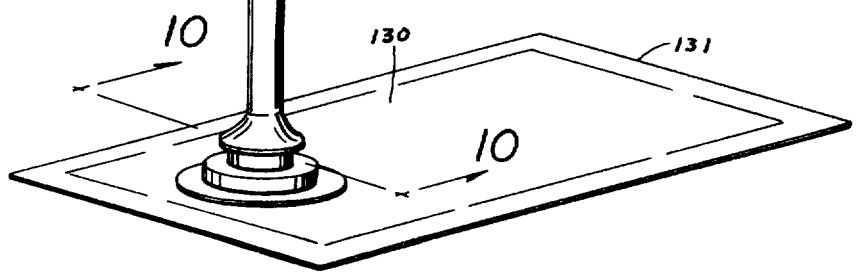
FIG. 9 is a perspective view of an expandable syringe embodying principles of the invention in yet another preferred form.

With reference next to FIGS. 9–11 an expandable syringe is shown in yet another form to comprise an elastic bag 130 having the flat illustrated shape in its relaxed state. One end 131 of the bag is open for bag filling and is provided with conventional zipper means or the like for closing once the bag is filled with liquid. A resilient backing ring 133 is permanently affixed to an interior surface of the bag. The syringe also includes a resilient coupler having a recess 135 sized to receive the backing ring and portion of the bag to which it is secured. The coupler has an internally threaded tubular throat 137 extending upwardly from recess 135, and a flat annular flange 139 extending laterally about the coupler recess lips 140. The syringe is further seen to include a nozzle 142 having a set of peripheral ports 144 formed in an end thereof distal the elastic bag and another externally threaded end 145 proximal the bag and coupler which has a sharply pointed tip 146.

In operation, the resilient coupler is snapped onto the elastic bag by pressing resilient ring 133 into the coupler recess 135 over recess lips 140. Water is then introduced into the open end 131 of the bag and the end closed. Nozzle 142 is then mounted to the coupler and bag by screwing end 145 into the coupler throat 137. This action brings nozzle tip 146 into puncturing contact with that portion 149 of the overlaying backing ring 133. Continued insertion of the nozzle tip brings nozzle flange 151 into engagement with coupler flange 153 and with nozzle end 145 fully into the punctured opening of the bag. Collapsing of the bag may then cause water to be expelled from the bag and nozzle.

It should be understood that the first described embodiments merely illustrate principles of the invention in selected, preferred forms. Many additions, deletions and changes may, of course, be made to these specifically described examples without departure from the spirit and scope of the invention as set forth in the following claims.

I claim:

1. An expandable syringe comprising an elastic bag having an opening through which liquid may pass; a resilient nozzle including a generally cylindrical tubular body defining a central passageway extending therethrough and a tip member removably mounted on a free end of said tubular body, said tip member having a plurality of radially spaced peripheral ports and a hollow hub extending axially within said tubular body and spaced from the inner surface of said tubular body, and a plurality of axially extending ribs joining said hub with said tubular body inner surface to define a plurality of axially extending channels providing fluid communication between said central passageway and said plurality of ports; and means for mounting said nozzle to said elastic bag with said central passageway in valve controllable fluid communication with said bag opening.

2. An expandable syringe in accordance with claim 1 wherein said nozzle tip member includes a generally cylindrical base portion disposed proximate to said tubular body member, and a rounded end portion disposed distal to said tubular body member and extending from said base portion, and wherein said plurality of radially spaced peripheral ports are formed in said nozzle tip cylindrical base portion.

3. An expandable syringe in accordance with claim 2 wherein the diameter of said tubular body member adjacent said tip member is smaller than the diameter of said tip cylindrical base portion whereby the liquid exiting said nozzle through said ports is generally directed about the nozzle tubular body member away from said nozzle tip rounded end portion.

4. An expandable syringe in accordance with claim 1 wherein said tip member includes a base portion disposed proximate said tubular body and a rounded end portion disposed distal to said tubular body and extending from said base portion, said peripheral ports being formed in said base portion of said tip member.

5. An expandable syringe in accordance with claim 4 wherein said tubular body has an annular end adjacent said base portion and bounding a portion of each said peripheral port.

6. An expandable syringe in accordance with claim 5 wherein the diameter of said tubular body at said annular end is smaller than the diameter of said tip base portion whereby the liquid exiting said nozzle is generally directed from said ports and away from said tip end portion.

7. A resilient, detachable nozzle for use with an expandable fluid receiving reservoir comprising:
 a generally cylindrical tubular body defining a central passageway extending therethrough;
 a tip member removably mounted on a free end of said tubular body and including a plurality of radially spaced peripheral ports;
 a hollow hub extending from said tip member axially within said tubular body, said hub being spaced from the inner surface of said tubular body;
 a plurality of axially extending ribs joining said hub with said tubular body inner surface to define a plurality of axially extending channels providing fluid communication between said central passageway and said plurality of ports; and
 means for detachably mounting said tubular body to said fluid receiving reservoir with said central passageway in valve controllable fluid communication with said reservoir.

* * * * *